(12) United States Patent
Moriwaki et al.

(10) Patent No.: US 7,540,538 B2
(45) Date of Patent: Jun. 2, 2009

(54) DIALYZER-CONNECTING COUPLER JOINT

(75) Inventors: Shouichi Moriwaki, Yokohama (JP); Makoto Mitsuhashi, Osaka (JP)

(73) Assignee: Nipro Corporation, Osaka (JP)

( * ) Notice: Subject to any disclaimer, the term of this patent is extended or adjusted under 35 U.S.C. 154(b) by 169 days.

(21) Appl. No.: 10/870,496

(22) Filed: Jun. 18, 2004

(65) Prior Publication Data
US 2005/0006297 A1    Jan. 13, 2005

(30) Foreign Application Priority Data
Jun. 19, 2003    (JP)    ............... 2003-174562

(51) Int. Cl.
*F16L 55/00*    (2006.01)
(52) U.S. Cl. ............... 285/86; 285/317; 210/321.6
(58) Field of Classification Search ............... 285/397, 285/398, 31, 370, 317; 210/321.6, 541, 646
See application file for complete search history.

(56) References Cited
U.S. PATENT DOCUMENTS

| 1,188,485 | A | * | 6/1916 | Pruyn | ............... | 285/397 |
| 2,090,266 | A |   | 8/1937 | Parker |   |   |
| 3,962,767 | A | * | 6/1976 | Byerley et al. | ............... | 285/370 |
| 4,236,736 | A | * | 12/1980 | Anderson | ............... | 285/398 |
| 5,316,352 | A | * | 5/1994 | Smith | ............... | 285/370 |
| 5,322,329 | A |   | 6/1994 | Michael |   |   |
| 5,507,535 | A | * | 4/1996 | McKamey et al. | ............... | 285/370 |

FOREIGN PATENT DOCUMENTS

| EP | 0 568 890 A1 | 4/1993 |
| GB | 861531 | 2/1961 |
| JP | 9-51945 A | 2/1997 |
| JP | 10-248924 | 9/1998 |
| JP | 2001-299907 A | 10/2001 |

* cited by examiner

*Primary Examiner*—Aaron Dunwoody
(74) *Attorney, Agent, or Firm*—Kubovick & Kubovcik

(57) ABSTRACT

A coupler joint (10) which includes a hollow cylindrical portion (11) opened at its opposite ends and a flange (12) disposed along the circumference of the cylindrical portion (11) near the longitudinal center to be interposed between a dialyzer connector (21) and a coupler (30) so as to be in liquid tight engagement; one side of the flange (12) of the coupler joint 10 being in liquid-tight abutment with an opening (22) of the connector (21) of the dialyzer (20), and the other side of the flange (12) being in liquid-tight abutment with the a seal surface 31 of the coupler (30). Accordingly, a dialysis solution does not collect in a concave groove (32) which accommodates an O-ring (40) of the coupler (30), and proliferation of bacteria can be prevented.

15 Claims, 6 Drawing Sheets

Prior Art

Prior Art

Prior Art

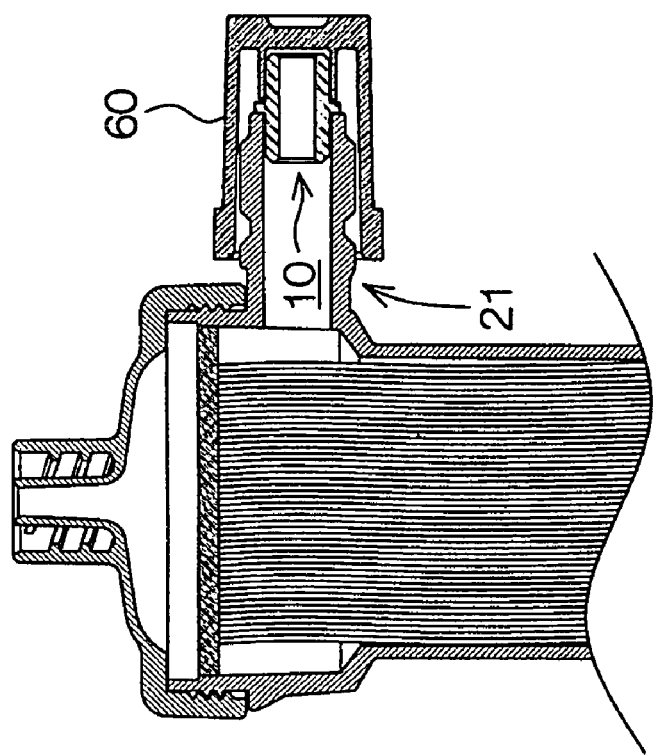
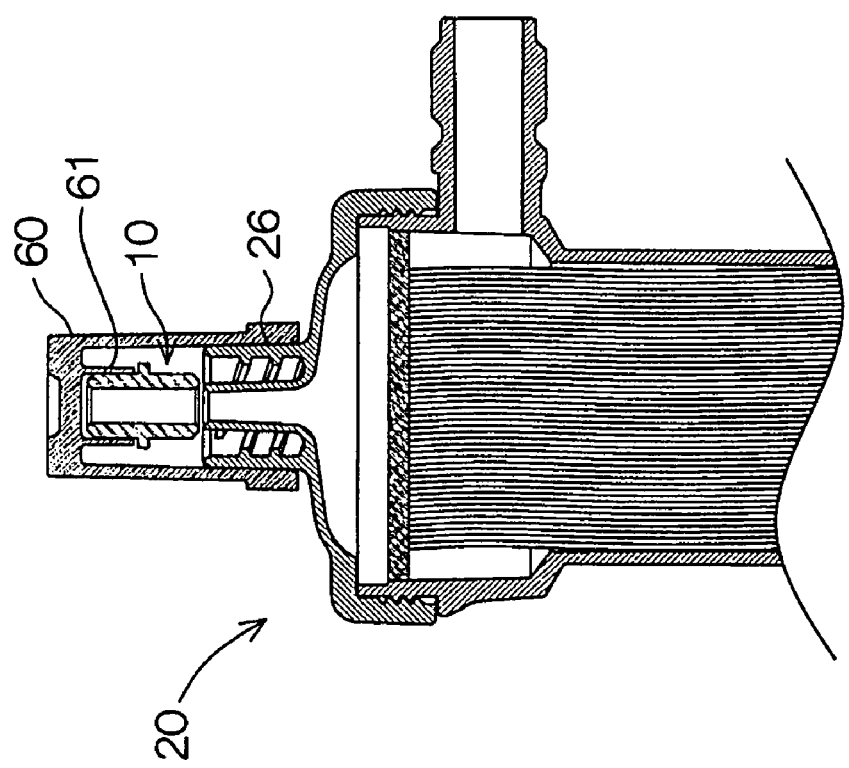

21A

DIALYZER-CONNECTING COUPLER JOINT

BACKGROUND OF THE INVENTION

1. Field of the Invention

The present invention relates to a coupler joint which can be interposed between a dialyzer connector and a coupler of dialysis apparatus when the connector and the coupler are to be connected to each other.

2. Description of the Related Art

Numerous people have recently been forced to undergo artificial dialysis owing to kidney dysfunction or the like. Artificial dialysis serves a part of the role of the kidneys, eliminating wastes from blood and adjusting water content, electrolytes and pH. In almost all artificial dialysis which is currently performed, hollow fiber dialyzers are used, and a dialyzer is connected to a dialysis apparatus which monitors and controls artificial dialysis. Blood flows inside approximately ten thousand hollow fibers which are charged in the dialyzer, while a dialysis solution flows outside the hollow fibers. Two solution supplying/discharging tubes which supply and discharge the dialysis solution to and from the dialyzer extend from the dialysis apparatus, and the tip of each of these solution supplying/discharging tubes is provided with a coupler to be connected to a connector which is a dialysis solution outlet/inlet for the dialyzer.

The dialyzer connector 21 shown in FIG. 2 has a shape determined by international standards (ISO8637). And the coupler which is connected to this connector, as shown in FIG. 3, has a plurality of components such as an O-ring 40, ball bearings 50 and a spring 80.

The dialyzer is disposable and is abandoned after the completion of artificial dialysis, but the dialysis solution circulating tubes and the coupler provided in the dialysis apparatus are cleaned and sterilized, and are repeatedly reused. However, this coupler, as mentioned above, is made of a plurality of components such as ball bearings and an O-ring, so that gaps are inevitably formed between the components, and dialysis solution enters these gaps during artificial dialysis. As shown in FIG. 5, the dialysis solution particularly easily enters the gap between the O-ring 40 and a concave groove 32, and if the dialysis solution in this portion is not fully cleaned during cleaning, bacteria are likely to propagate in this portion. Then, there is a risk that endotoxin produced by these bacteria enters the dialysis solution during dialysis and this endotoxin enters a blood of a patient being dialyzed.

To solve this problem, a seal position connecting a dialyzer connecter with a coupler during dialysis and a seal position connecting an adapter with the coupler during cleaning and sterilizing of the dialysis apparatus have been modified in a prior invention. (See Japanese laid-open publication No. JP 9-51945 A).

However, the coupler and the adapter described in JP 9-51945 A have exclusive special shapes, and cannot have the desired effect without such combination. Accordingly, if it is used in an incorrect combination, there is a risk that complete cleaning and sterilization cannot be effected.

BRIEF SUMMARY OF THE INVENTION

The inventors of the present invention, devoting themselves to research for solving the problems described above, have completed the present invention.

That is, the present invention relates to:

(1) A coupler joint to be interposed between a connector and a coupler connected to the connector so as to be liquid tight, comprising a hollow cylindrical portion opened at its opposite ends and a flange provided along a circumference of the cylindrical portion intermediate of the ends, said coupler joint having a structure such that when it is interposed between said connector and coupler one side of the flange is in liquid tight abutment with a surface at the opening of the connector, and the other end of the flange is in liquid tight abutment with the seal surface of the coupler, wherein the connector is a dialyzer connector and the coupler is a coupler provided at a tip of a solution supplying/discharging tube extending from a dialysis apparatus;

(2) A coupler joint according to (1), wherein one end of the cylindrical portion is adapted for insertion into the opening of the connector, and the other end of the cylindrical portion is adapted for insertion into a coupler joint inserting hole provided in the coupler, thus sandwiching the flange;

(3) A coupler joint according to (1), wherein the opposite ends of the cylindrical portion are tapered;

(4) A coupler joint according to (1), wherein the material forming the cylindrical portion is the same as the material forming the flange;

(5) A coupler joint according to (1), wherein the material forming the cylindrical portion is different from the material forming the flange;

(6) A coupler joint according to (1), wherein the flange is formed from a material having elasticity;

(7) A coupler joint according to (1), interposed between a header of a dialyzer and a header cap fitted on the header.

BRIEF DESCRIPTION OF THE DRAWINGS

FIG. 6 includes partially enlarged cross-sectional views showing states in which the coupler joint according to the invention is accommodated in a header cap. FIG. 6(a) is a partially enlarged cross-sectional view showing the state in which the coupler joint according to the invention is attached to a header together with the header cap. FIG. 6(b) is a partially enlarged cross-sectional view showing the state in which the coupler joint according to the invention is attached to the connector.

DETAILED DESCRIPTION OF THE INVENTION

Figure 1:
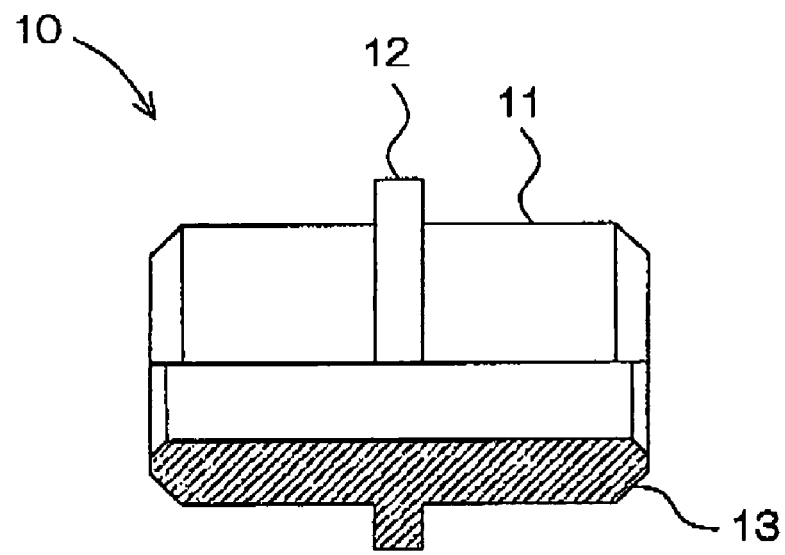
FIG. 1 is a partly cutaway, longitudinal sectional view of a coupler joint according to the invention.
Figure 4:
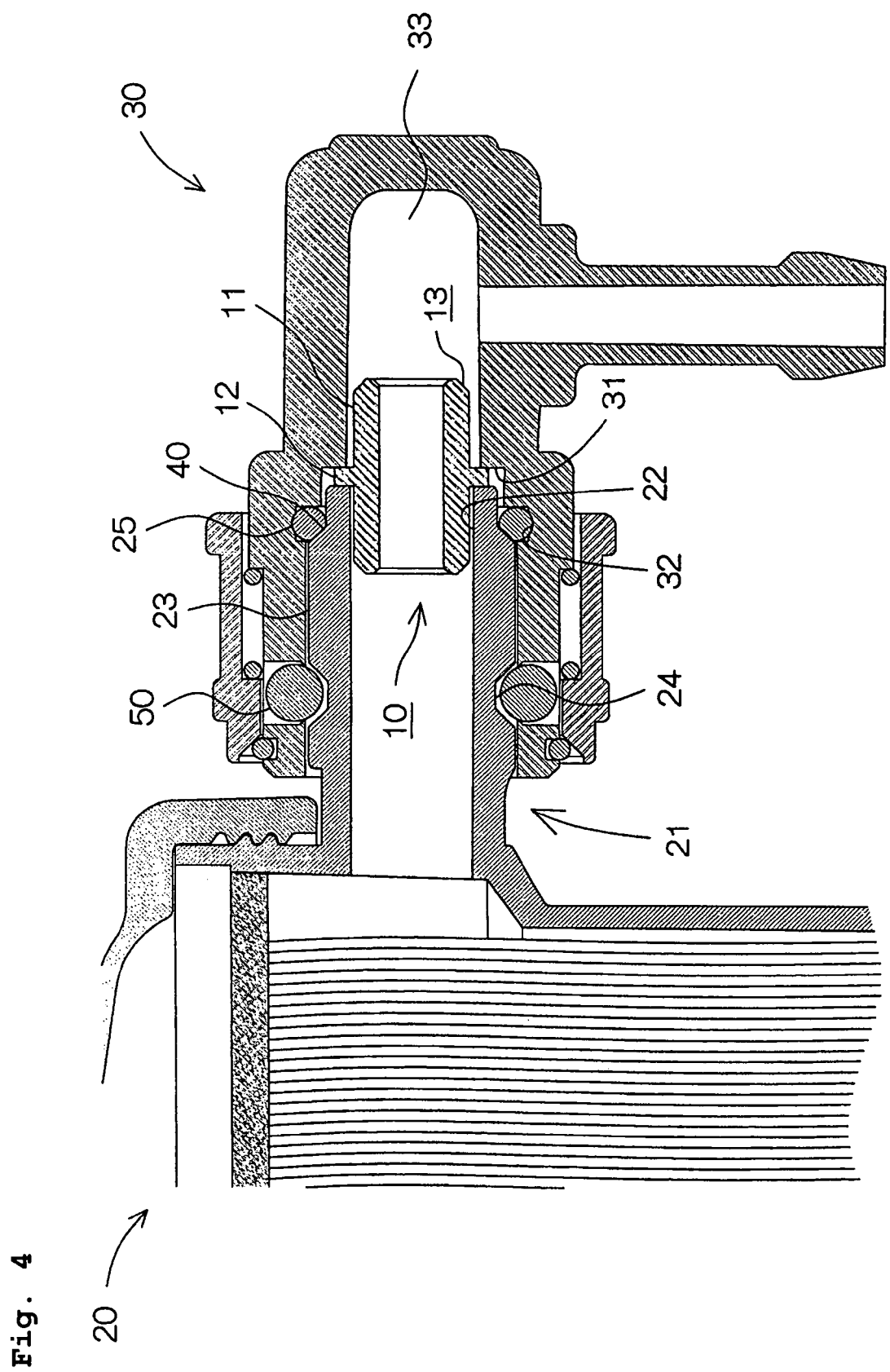
FIG. 4 is a partially enlarged cross-sectional view showing the state in which the coupler joint according to the invention is interposed between the connector of a dialyzer and the coupler so as to be liquid tight.
Figure 5:
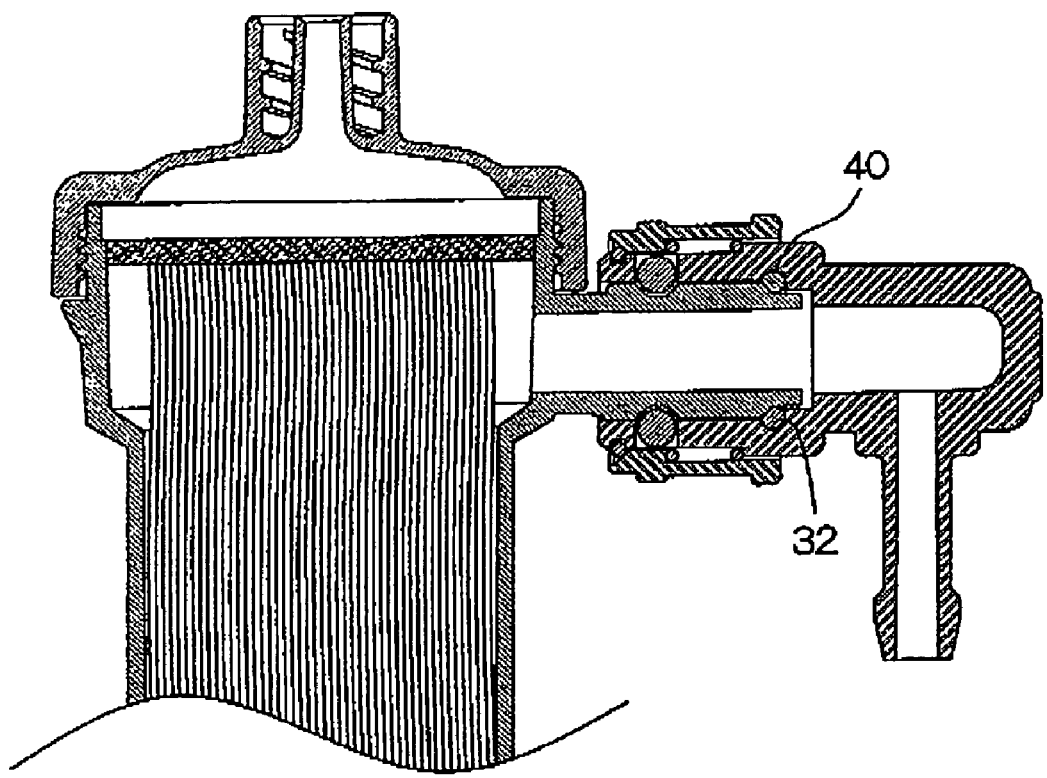
FIG. 5 is a partially enlarged cross-sectional view showing the state of a prior-art connection between the connector of a dialyzer and a coupler.

A coupler joint 10 according to the invention, as shown in FIG. 1, is constructed so that a hollow cylindrical portion, or member 11 is opened at its opposite ends and a flange 12 is circumferentially disposed at approximately the longitudinal center of the cylindrical portion 11, and, as shown in FIG. 4, is constructed so that when the coupler joint is interposed, one side of the flange 12 is in liquid-tight abutment with the opening portion 22 of a connector 21 of a dialyzer 20, and the other side of the flange 12 is in liquid-tight abutment with the seal surface 31 of a coupler 30. Accordingly, an O-ring 40 of the coupler 30 does not come into contact with a solution, for example, a dialysis solution, flowing in the coupler 30 and the connector 21, and the dialysis solution does not collect in the concave groove 32 which accommodates the O-ring 40.

The diameter of the cylinder portion of the coupler joint is preferably from 8.9 mm to 9.2 mm and, more preferably, from 9.0 mm to 9.1 mm and the outside diameter of the flange 12 is 1 mm or more larger than the diameter of the cylinder portion and the range of the diameter is preferably from 1 mm or more larger than the cylinder portion diameter up to a diameter of 13 mm.

The thickness of the wall of the cylindrical portion of the coupler joint is preferably, from 0.5 mm to 3 mm and, more preferably, from 0.5 mm to 1.5 mm The longitudinal thickness of the flange 12 is set so that the sides of the flange 12 respectively abut on the seal surface 31 and the tip portion of the connector 21 so as to be liquid tight, and ball bearings 50 of the coupler 30 which will be described later engage with an engagement groove 24 of the connector 21. The thickness is preferably 1.0 mm to 2.0 mm and, more preferably, 1.5 mm. If the flange 12 is thicker than 2.0 mm, the ball bearings 50 of the coupler 30 and the engagement groove 24 of the connector 21 cannot engage with each other. If the flange 12 is thinner than 1.0 mm, the end surface of the flange 12 cannot abut on the seal surface 31 so as to be liquid tight, and there is a risk that the flange 12 cannot be in liquid-tight abutment.

One end of the cylindrical portion 11 can be inserted into the opening 22 of the connector 21, and the other end can be inserted into a coupler joint inserting hole 33 provided in the coupler 30. The opposite ends of the cylindrical portion 11 have tapered portions 13, respectively. Accordingly, the coupler joint 10 can be easily inserted into the connector 21 and the coupler 30 and the header cap 60 of the dialyzer 20 which will be described later.

The longitudinal length of the end of the cylindrical portion of the coupler joint on the connector side of the flange is preferably from 3 mm to 10 mm. The length of the end of the cylindrical portion of the coupler joint on the coupler side of the flange is preferably from 5 mm to 11 mm.

As the material for forming the coupler joint 10, thermoplastic plastics such as polyethylene, polypropylene, mixtures of polyethylene and polypropylene, polycarbonate, polyethylene terephthalate, polyethylene terenaphthalate, polyvinyl alcohol, ethylene-vinyl alcohol copolymers, polyvinylidene chloride and nylon can be used, or elastic materials such as butyl rubber, chlorinated butyl rubber, thermoplastic elastomers and silicone elastomers can be used, but the kinds of materials are not particularly limited as long as they do not change even when they come into contact with dialysis solutions. Particularly in the case where an elastic material is used, the liquid-tightness among the coupler joint 10, the coupler 30 and the connector 21 becomes far higher, and during manufacture, even in the case where the connector, the coupler and the coupler joint have dimensional errors, they can be connected to one another with allowance for the errors.

Even in the case where the cylindrical portion 11 is formed of a thermoplastic plastic, only the flange 12 need be formed of the above-mentioned elastic materials (not shown). In this case as well, the liquid-tightness among the coupler joint 10, the coupler 30 and the connector 21 can be improved compared to the case where the flange 12 is formed of only a thermoplastic plastic. When this coupler joint is to be manufactured, the flange which has been formed of an elastic material may be fitted into a concave groove formed near the longitudinal center of the cylindrical portion, or may be formed by insert molding, or may also be formed by two-color molding.

Figure 2:
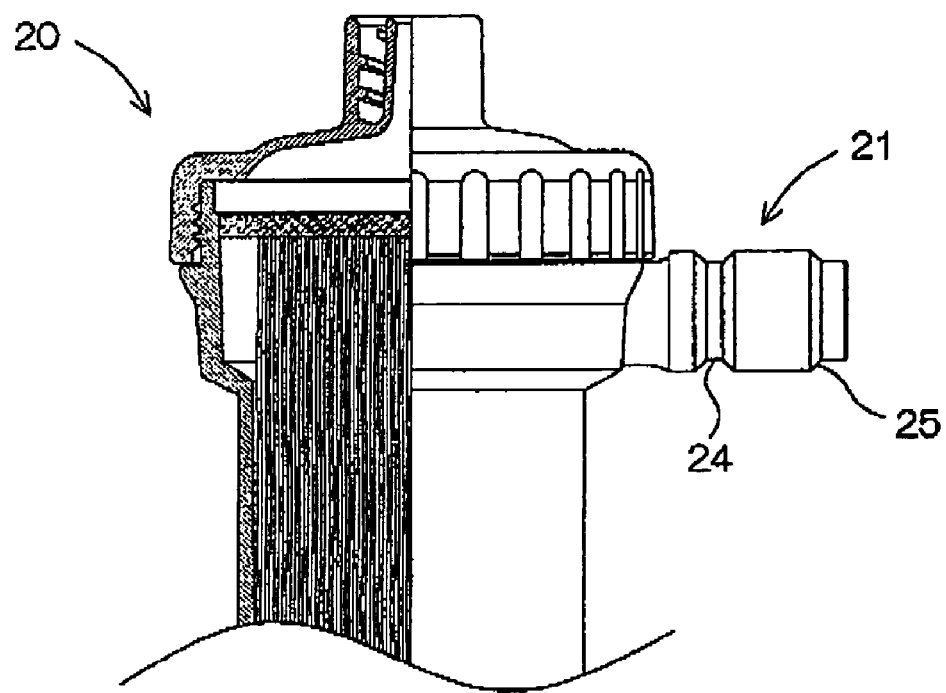
FIG. 2 is a partly cutaway, longitudinal sectional view of a dialyzer.

The dialyzer connector 21 of the dialyzer 20 shown in FIG. 2 has a shape determined by international standards (ISO 8637), and the connector 21 is provided with a taper 25 so that connector 21 can come into liquid-tight contact with the O-ring 40 in the coupler 30, and the engagement groove 24 is disposed along the circumference of the connector 21 near the longitudinal center. The ball bearings 50 disposed at a plurality of locations on the inner circumferential surface of the coupler 30 are brought into engagement with the engagement groove 24 of the connector 21, so that the connector 21 and the coupler 30 do not disengage.

Figure 3:
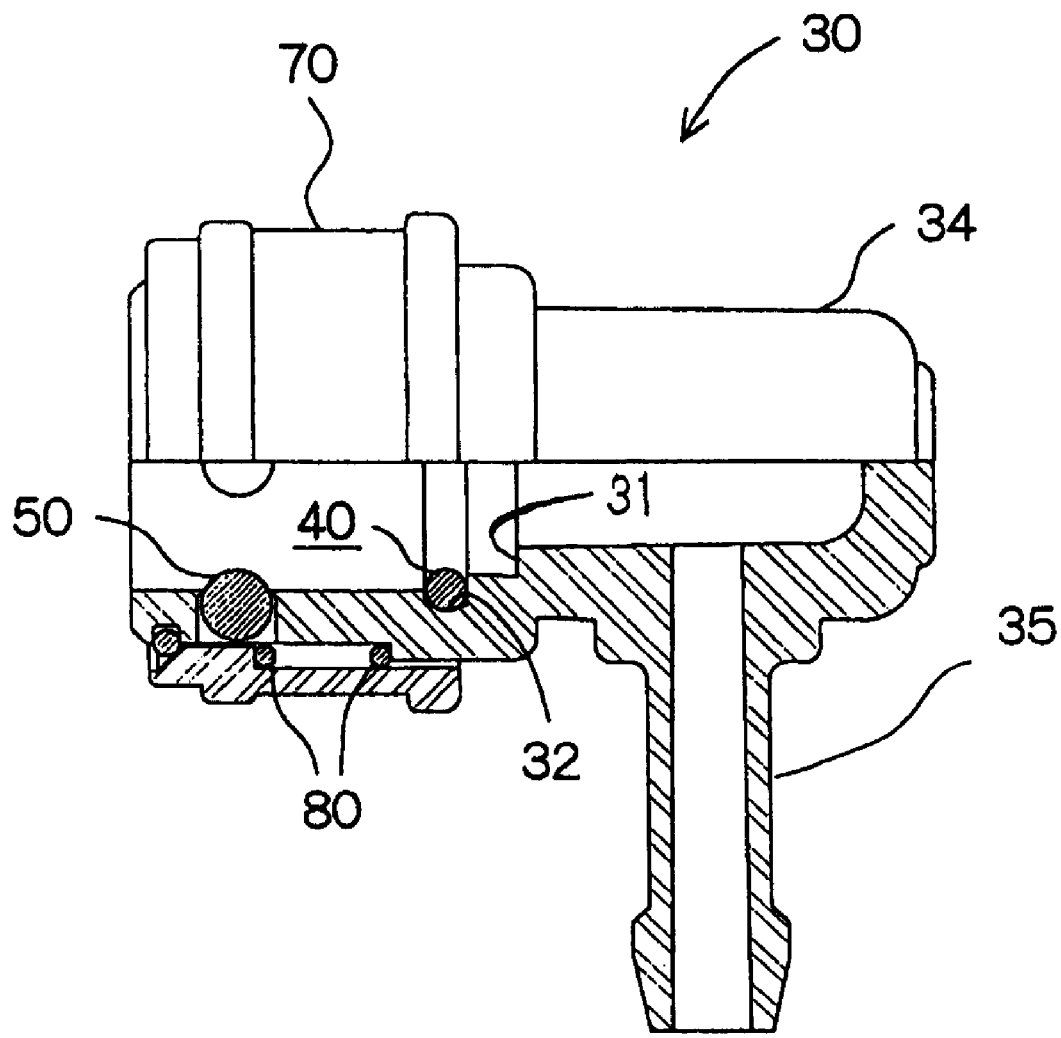
FIG. 3 is a partly cutaway, longitudinal sectional view of a coupler.

A coupler body 34 of the coupler 30 as shown in FIG. 3 has an opening portion to engage with the dialyzer connector 21, and a nozzle 35 to which a solution supplying/discharging tube (not shown) can be connected, and is mainly formed of a metal material such as stainless steel or a plastic material such as polyethylene or polypropylene. On the inner circumferential surface of the coupler body 34, ball bearings 50 for engaging with the engagement groove 24 of the connector 21 are disposed at a plurality of locations on the inner circumferential surface, and the concave groove 32 which accommodates the O-ring 40, on which the taper 25 of the muffler 23 of the connector 21 is to abut, is also provided. In addition, a sleeve 70 which is movable back and forth and controls the radial movement of the ball bearings 50 and a spring 80 which restricts the movement of the sleeve 70 are provided on the outer circumferential surface of the coupler body 34. When the sleeve 70 is moved backward against the elastic force of the spring 80, the ball bearings 50 become able to move outwardly in the radial direction so that the connector 21 can be inserted into the coupler 30. When the sleeve 70 is moved forward, the ball bearings 50 become unable to move and engage with the engagement groove 24 of the connector 21. It is to be noted that the connector 21 and the coupler 30 need not have special shapes provided that the coupler joint 10 is inserted, and can be conventional products which have heretofore been used. In this manner, the invention is also characterized in that the connector 21 and the coupler 30 can be existing products without any modification.

In addition, the coupler joint 10 according to the invention can be provided in the state of being interposed between a header 26 to which a blood circuit is to be connected and a header cap 60 fitted on the header 26, as shown in FIG. 6(a). The coupler joint 10 which is provided in this manner is removed from the header 26 integrally with the header cap 60, and is fitted as-is onto the connector 21 as shown in FIG. 6(b), and after that, when the header cap 60 is removed, only the coupler joint 10 is fitted in the connector 21. At this time, since a hand or a finger comes into contact with only the header cap 60 in which the coupler joint 10 is accommodated, the coupler joint 10 can be prevented from being contaminated with bacteria adhering to the hand or the finger. Although the coupler joint 10 is fitted into a skirt 61 in the header cap 60, it is preferable that the force required to remove the coupler joint 10 from the skirt 61 be set smaller than the force required to remove the coupler joint 10 from the connector 21 so that the coupler joint 10 is prevented from coming off when the header cap 60 is removed after the coupler joint 10 has been attached to the connector 21.

Although in FIG. 6(a) the header 26 is a luer lock, the shape is not particularly limited as long as it can be connected to a blood circuit. As the material forming the header cap 60, thermoplastic plastics such as polyethylene, polypropylene, mixtures of polyethylene and polypropylene, polycarbonate, polyethylene terephthalate, polyethylene terenaphthalate, polyvinyl alcohol, ethylene-vinyl alcohol copolymers, polyvinylidene chloride and nylon can be used, or elastic materials such as butyl rubber, chlorinated butyl rubber, thermoplastic elastomers and silicone elastomers can be used. The kinds of forming materials are not particularly limited as long as they are known as materials useful for forming components of medical instruments.

As is apparent from the foregoing description, according to the invention, it is possible to prevent the interiors portions of a connector of a dialyzer and a coupler from being contaminated by microorganisms and bacteria, without modifying either the connector of a dialyzer which has heretofore been used or the coupler to be connected to the connector. In addition, a coupler joint according to the invention is provided in a state capable of being accommodated in the header cap of a header of a dialyzer, without the need to modify the connector or the coupler. In addition, the coupler joint according to the invention is provided in a state capable of being accommodated in the header cap of a header of a dialyzer, so that there is no risk that the coupler joint is lost, and in use, there is no need to search for the coupler jack. In addition, the coupler joint can be aseptically fitted into the connector without being touched by a hand, a finger or the like.

Figure 7A:
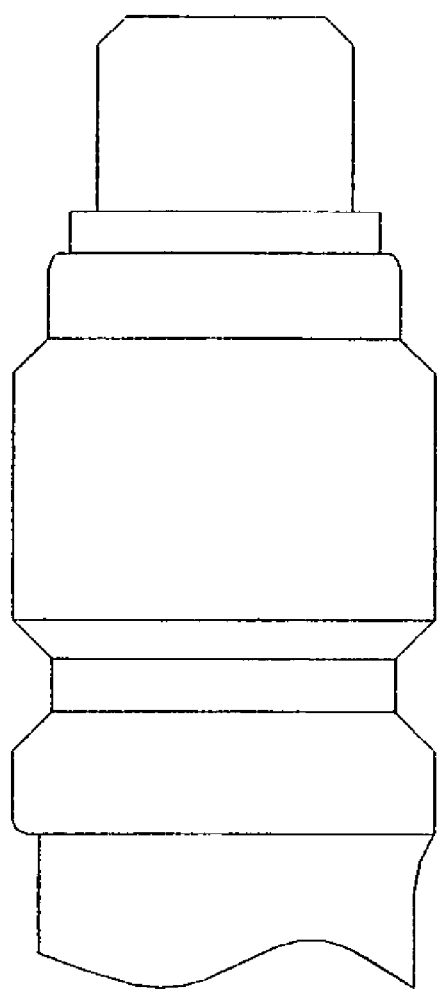
FIGS. 7(a) and 7(b) are partially enlarged cross-sectional views of a dialyzer connector according to another aspect of the present invention in which the flange and a cylindrical portion of the coupler joint are integrally formed with the dialyzer connector.
Figure 7B:
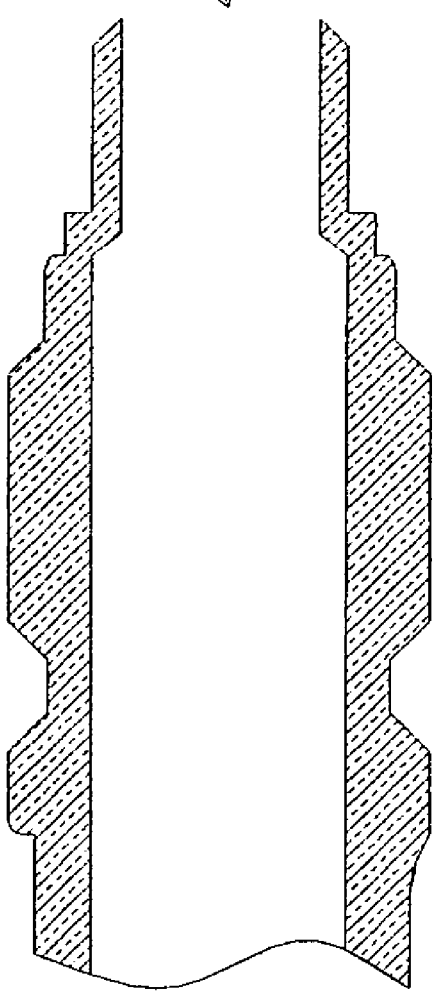

According to another aspect of the present invention as shown in FIGS. 7(a) and (b), a dialyzer connector 21A is provided in which the flange and an end of the cylindrical portion of the coupler joint are integrally formed as part of the connector. FIG. 7(a) is a cross-sectional view of the connector 21A and FIG. 7(b) is a front-view of the connector 21A.

What is claimed is:

1. A coupler joint to be interposed between a connector and a coupler connected to the connector so as to be liquid tight, wherein the connector is a dialyzer connector and the coupler is a coupler provided at a tip of a solution supplying/discharging tube extending from a dialysis apparatus, the coupler joint consisting of a hollow cylindrical portion opened at its opposite ends and a flange provided along a circumference of the cylindrical portion, said coupler joint having a structure such that one end of the coupler joint is dimensioned and configured to be inserted into an opening of the connector and the other end is dimensioned and configured to be inserted into an opening of the coupler, and such that when said coupler joint is interposed between said connector and coupler one side of the flange is in liquid tight abutment with a surface at the opening of the connector, and the other end of the flange is in liquid tight abutment with the seal surface of the coupler;
    wherein the coupler has a sleeve and at least one ball bearing for engaging the connector,
    the connector has a groove for engaging the ball bearing, and
    when the sleeve is moved backward, the at least one ball bearing moves outwardly in the radial direction so that the connector can be inserted into the coupler.

2. A coupler joint according to claim 1, wherein one end of the cylindrical portion is dimensioned and configured for insertion into the opening of the connector, and the other end of the cylindrical portion is dimensioned and configured for insertion into a dialysis connector inserting hole provided in the coupler, thus sandwiching the flange.

3. A coupler joint according to claim 1, wherein the opposite ends of the cylindrical portion are tapered.

4. A coupler joint according to claim 1, wherein a material forming the cylindrical portion is the same as a material forming the flange.

5. A coupler joint according to claim 1, wherein the flange is formed from a material having elasticity.

6. A combination of a header of a dialyzer and a coupler joint according to claim 1 which is removably fitted on the header, the coupler joint being adapted to be removed from the header and interposed between a connector of the dialyzer and a coupler connected to the connector so as to be liquid tight.

7. A dialyzer connector in which the flange and an end of the cylindrical portion of the coupler joint of claim 1 are integrally formed as part of the connector, said end being dimensioned and configured for insertion into a dialysis connector inserting hole provided in a coupler provided at a tip of a solution supplying/discharging tube extending from a dialysis apparatus.

8. A coupler joint according to claim 2, wherein the opposite ends of the cylindrical portion are tapered.

9. A coupler joint according to claim 2, wherein a material forming the cylindrical portion is the same as a material forming the flange.

10. A coupler joint according to claim 3, wherein a material forming the cylindrical portion is the same as a material forming the flange.

11. A coupler joint according to claim 4, wherein the flange is formed from a material having elasticity.

12. A coupler joint according to claim 1, wherein the diameter of the cylindrical portion is from 8.9 mm to 9.2 mm.

13. A coupler joint according to claim 1, wherein the outside diameter of the flange is 1 mm or more larger than the diameter of the cylindrical portion.

14. A coupler joint according to claim 13, wherein the outside diameter of the flange is from 1 mm or more larger than the diameter of the hollow cylindrical portion to 13 mm.

15. A coupler joint to be interposed between a connector and a coupler connected to the connector so as to be liquid tight, consisting of a hollow cylindrical portion opened at its opposite ends and a flange provided along a circumference of the cylindrical portion, said flange having a thickness of from 1.0 to 2.0 mm and said coupler joint having a structure such that when it is interposed between said connector and coupler one side of the flange is in liquid tight abutment with a surface at the opening of the connector, and the other end of the flange is in liquid tight abutment with the seal surface of the coupler, wherein the connector is a dialyzer connector and the coupler is a coupler provided at a tip of a solution supplying/discharging tube extending from a dialysis apparatus;
    wherein the coupler has a sleeve and at least one ball bearing for engaging the connector,
    the connector has a groove for engaging the ball bearing, and
    when the sleeve is moved backward, the at least one ball bearing moves outwardly in the radial direction so that the connector can be inserted into the coupler.

* * * * *